United States Patent [19]
Hardy

[11] Patent Number: 5,209,241
[45] Date of Patent: May 11, 1993

[54] PROPHYLACTIC DEVICE FOR A FEMALE

[76] Inventor: Betty J. Hardy, 2934 Moyers Rd., Richmond, Calif. 94806

[21] Appl. No.: 891,634

[22] Filed: Jun. 1, 1992

[51] Int. Cl.⁵ ............................ A61F 6/02; A61F 6/04
[52] U.S. Cl. ...................................... 128/842; 128/844
[58] Field of Search ........ 128/842, 844, 918, 830–841; 604/347–353, 330

[56] References Cited

U.S. PATENT DOCUMENTS

| | | | |
|---|---|---|---|
| 2,591,783 | 4/1952 | Craddock | 128/842 |
| 3,130,721 | 4/1964 | Young | 128/844 |
| 4,031,897 | 6/1977 | Graetz | 604/347 |
| 4,862,901 | 9/1989 | Green | 128/844 |
| 4,945,923 | 8/1990 | Evans | 128/842 |
| 4,981,147 | 1/1991 | Barnett | 128/842 |
| 4,993,431 | 2/1991 | Reddy | 128/918 |
| 4,993,433 | 2/1991 | Reddy | 128/844 |
| 4,997,427 | 3/1991 | Bowen | 604/349 |
| 5,036,863 | 8/1991 | Wheeler | 128/918 |
| 5,083,414 | 1/1992 | Wu | 128/844 |

*Primary Examiner*—Robert A. Hafer
*Assistant Examiner*—Michael Brown
*Attorney, Agent, or Firm*—Benman & Collins

[57] ABSTRACT

A prophylactic device is disclosed that can be utilized by a female. The device is a panty that includes upper and lower portions. The upper portion includes a velcro like fastener to allow the panty to be securely fastened to the user. The lower portion includes a tubular hourglass shape which is adapted to be inserted into a vaginal area of the user. The tubular portion also includes a coil member for locking the tubular portion with the pubic bone of the user.

4 Claims, 2 Drawing Sheets

PROPHYLACTIC DEVICE FOR A FEMALE

1. FIELD OF THE INVENTION

The invention relates generally to contraceptive and/or prophylactic devices and more particularly to those which provide barriers against bodily fluid transmission.

2. BACKGROUND OF THE INVENTION

Acquired Immune Deficiency Syndrome (AIDS) threatens the future of the human race. As is well known this disease is spread through blood by sharing of needles, by intravenous drug users, through blood transfusions or through sexual activity from a person who is infected.

It has become clear that the greatest risks to the human race is through transmission of the disease through sexual activity. Hence, to control the spread of the disease, the use of prophylactic devices (i.e. condoms) has been encouraged to prevent the sexual transmission of the virus. Despite repeated warnings, many men with active sex lives have shunned the use of these devices.

There are several reasons why there is a negative attitude toward condom usage. A first reason is the interruption of the natural sequence of sexual foreplay to apply the condom and the inconvenience of the removal requirements. Another factor is the conflicting opinions of medical authorities as to their effectiveness in preventing the transmission of the virus. Further, some health experts have stated that the average male does not properly apply or use condoms. Finally, certain condoms were permeable to the AIDS virus and could not be relied upon as an effective preventative.

Another problem with conventional methods for prevention is that condoms are typically for men. Since men do not traditionally like to use condoms, women are at their mercy. It is known that it is 20 times more likely for a female to be infected by the virus through heterosexual conduct than a man. Hence, it is imperative that women have a method for protecting themselves from this fatal disease that is not dependent upon a male using a condom.

Prophylactic devices for females are known in the art. For example, U.S. Pat. No. 4,862,901 teaches a prophylaxis that is configured as wearing apparel for the apparatus includes an upper fabric portion and a lower portion. The lower portion includes a closed end tubular portion which is adapted to be inserted in the vaginal cavity of the women.

Although this device would work adequately for its intended purpose, it has two major problems. Firstly this type of prophylaxis may not be comfortable for the female because the tubular portion can move around in the vaginal area of the female causing irritation and the like. Secondly the straight tubular portion of this patent may not provide feeling of pleasure to the female when sexual intercourse takes place. As has been mentioned above both of these problems will discourage females from using the device.

Hence, what is needed is a prophylactic device for a female that is easy to use and protects the female from sexually transmitted diseases such as AIDS or the like. In addition, this device should solve the above-mentioned problem of the female relying on the male for protection from these diseases. Finally, this device should be more comfortable and more pleasurable for the female than previously known devices.

DETAILED DESCRIPTION OF THE DRAWING

The present invention relates to an improvement in prophylactic devices for females. The following description is presented to enable one of ordinary skill in the art to make and use the invention and is provided in the context of a particular application and its requirements. Various modifications to the preferred embodiment will be readily apparent to those skilled in the art, and the generic principles defined herein may be applied to other embodiments. Thus, the present invention is not intended to be limited to the embodiments shown, but is to be accorded the widest scope consistent with the principles and features described herein.

Figure 1:
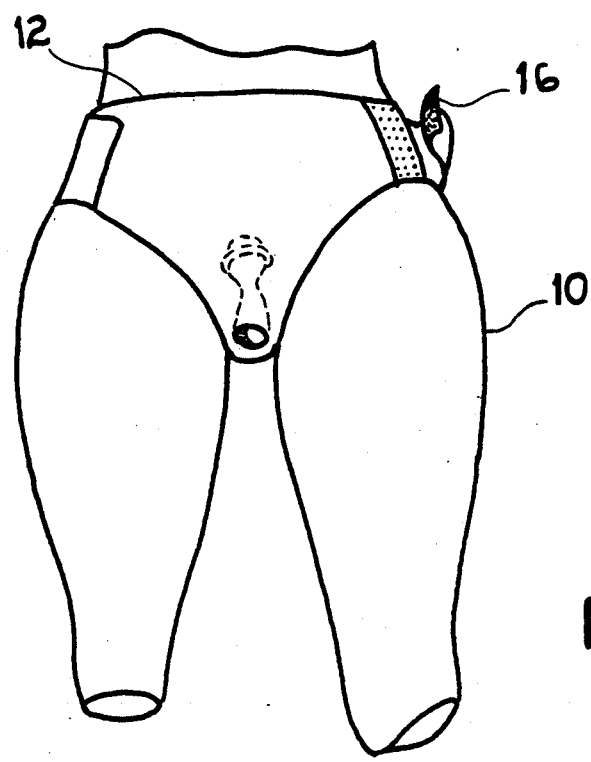
FIG. 1 is a perspective of the prophylactic device of the prevent invention on the torso of a female.

Referring now to FIG. 1, what is shown is a perspective view of the prophylactic device 10 on the torso of a female user of the present invention. In this embodiment the prophylactic device 10 comprises a first portion 12. The first portion 12 includes an attachment means 16 for securing the prophylactic device 10 to the torso of the female user. The prophylactic device 10 is made of material that is impervious to fluid transmissions so as not to transmit any sexually transmitted viruses.

Figure 2:
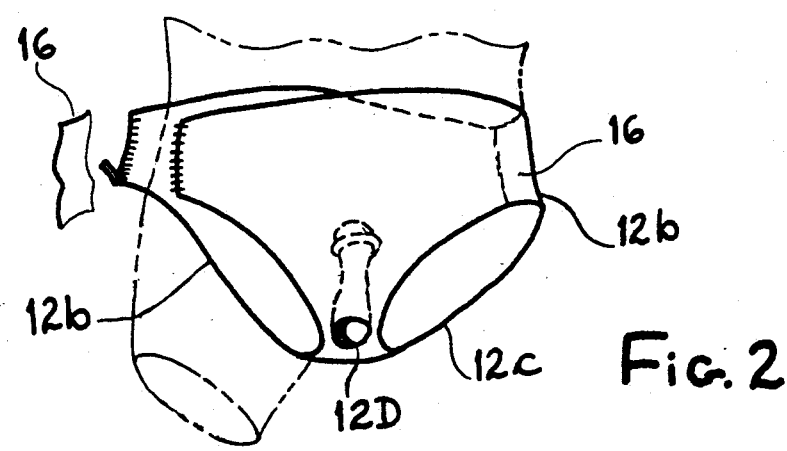
FIG. 2 is a diagrammatic view of the present invention.

FIG. 2 shows a diagrammatic view of the prophylactic device 10. The device includes a first portion 12. The first portion 12 includes front, back, side, and middle sections (12a–12d respectively). The first portion 12 as before described included an attachment means 16, in this case a two velcro fasteners located at a side section 12c thereof for allowing the upper portion to fit snugly over the torso of a user. The device 10 also includes a tubular portion 20 which is coupled to the middle section 12d of the first portion 12. The tubular portion 20 is adapted to fit within the vaginal area of the user. The tubular portion 20 in this embodiment is shaped in a hour-glass configuration to improve the sensitivity of the female when inserted into the vaginal area of the female.

Figure 3:
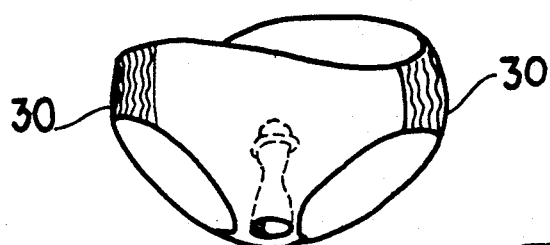
FIG. 3 is a diagrammatic view of a second embodiment of the present invention.
Figure 4:
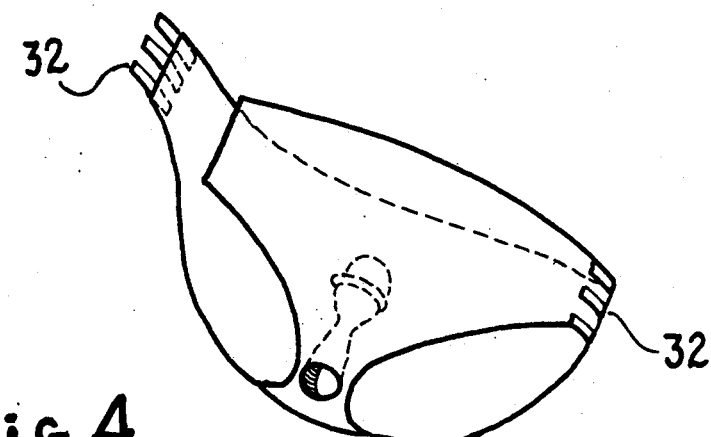
FIG. 4 is a diagrammatic view of a third embodiment of the present invention.

Although in this embodiment, two velcro fasteners 16 are shown as the attachments means, there are many types of fasteners could be utilized and that use would be within the spirit and scope of the present invention. For example, referring now to FIGS. 3 and 4 which show substantially the same device 10 as in FIGS. 1 and 2, an elastic type fastener 30 and a tape-like fastener 32 are shown respectively. Although, specific embodiments of attachment means are shown in FIGS. 2 through 4, there are many others that may be within the spirit and scope of the present invention.

Figure 5:
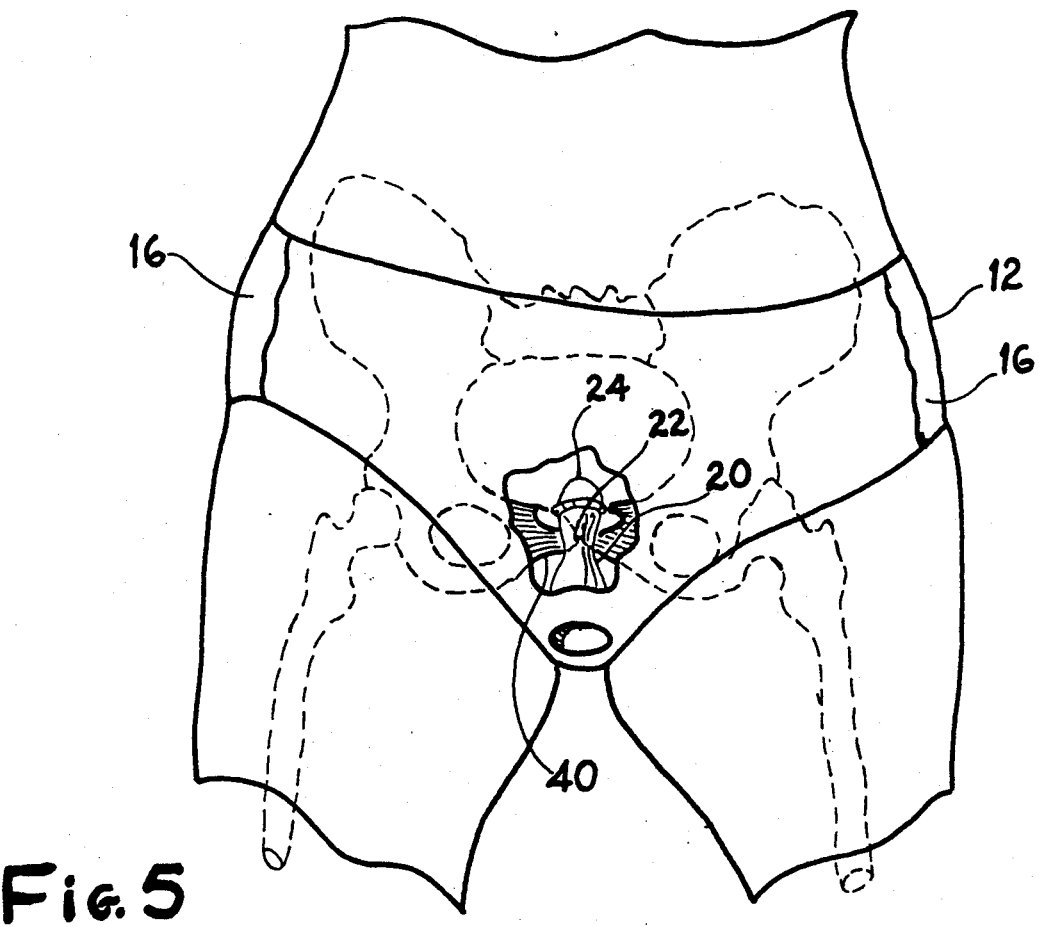
FIG. 5 shows the position of the tubular portion of the present invention in the vaginal area of the female.

Referring now to FIG. 5, the tubular portion 20 includes a coil member 22 which fits over a dome like member 24 of the tubular portion 20. This coil member 22 is adapted to lock into place with the pubic bone 40 and over the cervical area 42 (FIG. 5) of the female to ensure that the dome like member 24 of the tubular portion 20 is secure within the female. In so doing the prophylactic device 10 will be more comfortable to the female.

Through the use of this prophylactic device 10, a female can protect herself from sexually transmitted viruses. The device 10 also provides for a simple to use panty that can be adjusted to fit any user due to the attachment means. The device 10 fits securely within the female due to the interaction of the coil member 22 and dome member 24 with the pubic bone of the female. Finally, the device 10 can be easily manufactured due to its simple construction.

Although, the present invention has been described in accordance with the specific embodiments shown in FIGS. 1 through 5, one of ordinary skill in sort recognizes that there could be variations to the embodiment and those variations would be within the spirit and scope of the present invention. For example, the attachment means could be an elastic connector or the like and that use would be within the spirit and scope of the present invention. Similarly the hour-glass shape of the tubular portion 20 shown in the Figures could be changed to a different shape that improves sensitivity and that change is within the spirit and scope of the present invention.

These and other modifications may be made by those of ordinary skill in the art without departing from the spirit and scope of the present invention, the scope of which is defined solely by the appended claims.

What is claimed is:

1. An unitary apparatus for contraception and prophylactic enhancement for use by a female user comprising:
    a first portion to fit over the torso of a female user, the first portion having a front, back, side and middle section,
    an attachment means at the side section of the first portion for allowing for a snug fit of the first portion on the user;
    a hollow tubular portion coupled to the middle section of the first portion, the tubular portion being able to be inserted into the vaginal area of the user, the hollow tubular portion including a dome member that covers the cervical area of the female user; and
    means projecting outwardly from the tubular portion for securing the dome member behind the pubic bone of the female user.

2. The apparatus of claim 1 in which the attachment means comprises first and second hook and loop fasteners attached to the side section thereof.

3. The apparatus of claim 1 in which the hollow tubular portion is in s hour-glass configuration.

4. The apparatus of claim 1 in which the securing means is a coil member which is attached to the dome member.

* * * * *